US010262106B2

(12) United States Patent
Mansour

(10) Patent No.: US 10,262,106 B2
(45) Date of Patent: *Apr. 16, 2019

(54) VISUAL CHARTING METHOD FOR CREATING ELECTRONIC MEDICAL DOCUMENTS

(75) Inventor: Richard P. Mansour, Shreveport, LA (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 406 days.

This patent is subject to a terminal disclaimer.

(21) Appl. No.: 13/621,087

(22) Filed: Sep. 15, 2012

(65) Prior Publication Data

US 2013/0073314 A1 Mar. 21, 2013

Related U.S. Application Data

(63) Continuation of application No. 12/930,132, filed on Dec. 28, 2010, now abandoned.

(51) Int. Cl.
| | |
|---|---|
| *G06F 3/048* | (2013.01) |
| *G06T 15/00* | (2011.01) |
| *G06K 9/00* | (2006.01) |
| *G06F 19/00* | (2018.01) |
| *G06Q 50/24* | (2012.01) |
| *G16H 15/00* | (2018.01) |

(52) U.S. Cl.
CPC ........... *G06F 19/321* (2013.01); *G06Q 50/24* (2013.01); *G16H 15/00* (2018.01)

(58) Field of Classification Search
CPC ........ G16H 50/20; G16H 10/60; G16H 50/50; G06F 19/321; G06F 19/00; G06F 19/324; G06Q 50/24
USPC ........................................................ 705/2, 3
See application file for complete search history.

(56) References Cited

U.S. PATENT DOCUMENTS

2010/0316276 A1* 12/2010 Torti .............................. 382/131
2011/0082710 A1* 4/2011 Subash et al. .................... 705/3

* cited by examiner

*Primary Examiner* — Maroun P Kanaan
(74) *Attorney, Agent, or Firm* — Loza & Loza, LLP; Peter Zura

(57) ABSTRACT

A method of creating medical documentation uses selection of images representing synonyms for complex medical concepts. The images can be of two types, one corresponding to a parameter or Key in a Key/Value pair and the other corresponding to possible values of the selected parameter or Key. The user first selects an image or portion thereof corresponding to the parameter they wish to record observations, such as the heart or a valve of the heart. A set of images representing possible values of the parameter is then displayed e.g., images representing possible murmurs the selected valve may have. The user selects the image representing the value corresponding to the observation of the patient. A document is created by recording either the Key/Value image pairs or, alternative, text representing the synonyms for the images. Other methods of recording the document are possible, such as instantiating a set of class objects.

20 Claims, 12 Drawing Sheets

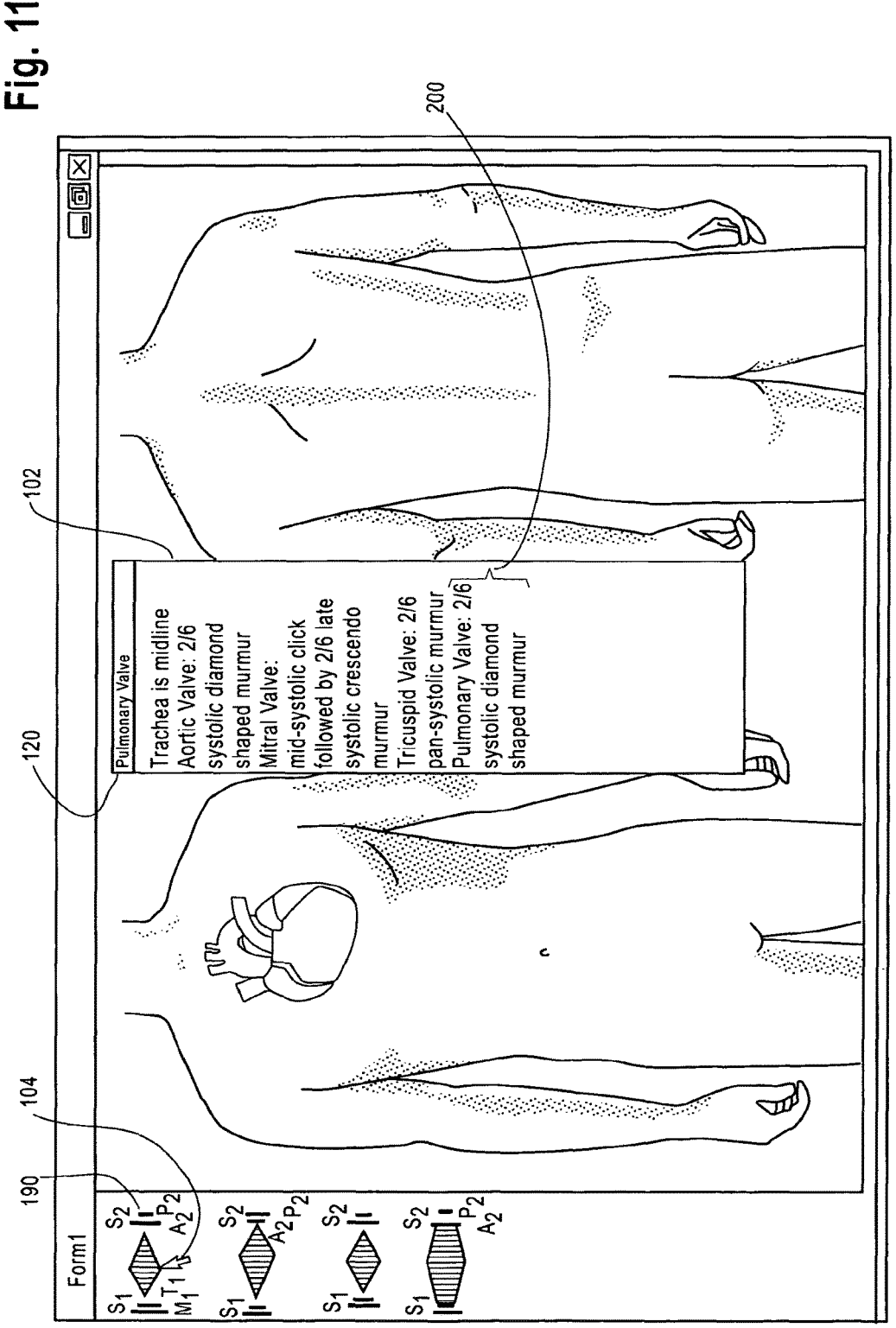

VISUAL CHARTING METHOD FOR CREATING ELECTRONIC MEDICAL DOCUMENTS

CROSS-REFERENCE TO RELATED APPLICATION

The present application is a U.S. continuation patent application of, and claims priority under 35 U.S.C. § 120 to, U.S. nonprovisional patent application Ser. No. 12/930,132, filed Dec. 28, 2010, which nonprovisional patent application published as U.S. patent application publication no. 2012/0166219, which patent application and any patent application publications thereof are incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

1. Field

This invention relates generally to the field of computerized systems for storing and creating electronic records, and in particular to methods and systems for creating medical documentation regarding a patient.

2. Description of Related Art

In the medical arena, hand written patient record keeping systems have evolved through many years of careful refinement and enhancement into systems which maintain a detailed manual record of medical information concerning each patient. To meet the needs of different hospital entities (such as doctors, nurses, pharmacy, accounting, laboratory, etc.) a manual record keeping system often requires that one piece of information be entered into multiple records. In addition it often requires that the same information that has not changed from visit to visit (such as family/social history, allergies, immunization status) be re-asked of the patient and re-documented in the current record. In certain instances, such as in the Emergency Department, this information may be asked and recorded as many as three separate times (on the Triage Note; the main ED record; and MD documentation) leaving the patient to wonder if there is any communication between healthcare providers and frustrating those healthcare providers who must fill out more and more paperwork. If the patient is admitted, this same information is then asked and recorded again by the admitting nurse and attending physician.

In a typical manual patient record keeping system a patient chart, usually in the form of a notebook, is maintained at the nursing station for each patient. The notebook is divided into a plurality of individual tabbed sections, such as Physicians Orders, Kardex, Nursing Care Plan, Nursing Assessment, and Laboratory.

Each of the above sections is further subdivided into a number of forms. The forms are those which are appropriate to the individual patient and/or such patient's physician. For example, within the Laboratory section there may appear forms for chemistry, hematology, blood gas, and microbiology.

In addition, a "flowsheet" chart is usually kept at the patient's bedside, particularly in a critical care environment. On the "flowsheet" chart there are individual areas for medication records, vital signs, intake/output, laboratory results, and other categories which are dependent upon the patient's affliction, such as intravenous (IV) drips.

Referring in particular to nursing functions, annotations to charts and/or nursing progress notes are made manually. Typically, brief notations are jotted down in various places through-out a shift. Sometime during the shift, typically at the end, the nurse makes a full notation into the nursing progress notes based on the brief notations or remembered items. This process can be very inefficient since notations may be forgotten or not copied appropriately. In particular, documentation and entry of physician orders, prescriptions and other activity has been viewed as two separate activities or steps, one step completing the documentation and a second step of entry of the order or prescription in the medical records of the patient.

The need for more efficiency of workflow and coordination between multiple departments and healthcare providers in a hospital environment has led to the advent of computerized medical records applications. Medical records management systems are known in the art and include the systems disclosed in the following U.S. Pat. Nos. 5,325,478; 5,247,611; 5,077,666; 5,072,383 and 5,253,362 all assigned to the assignee of this invention, and have been commercialized by the Assignee of this invention and others. Other background prior art of interest includes Cantlin et al., US 2006/0173858; Kim et al. U.S. Pat. No. 7,793,217; Britton et al. U.S. 2004/0015778 and Goede et al. U.S. Pat. No. 7,453,472.

Some software applications for creating medical documentation require a user to type in textual entries representing observations of a patient. Often, such observations may encompass complex medical concepts. As one example, in the context of a examination of a cardiac patient, the observations may include observations about particular heart murmur patterns present in the aortic, tricuspid, mitral and pulmonary valves. Medical documentation (e.g., a structured note) is created by the physician that documents all such observations. A text-based approach to creating such documentation (i.e., typing in all of the clinical observations) is time consuming and inefficient.

SUMMARY OF THE INVENTION

This invention meets a long-felt need in the art for a method for creating medical documentation more quickly than traditional text-based approaches. In particular, this invention provides a visual, symbolic approach to creating documents, referred to herein as "visual charting." In visual charting, complex medical concepts are presented on a user interface display as symbols which are selected by the physician as part of a medical documentation creation process. The symbols are, in essence, synonyms for a textual description of the complex medical concept. By means of selection of symbols, and in preferred embodiments a sequence of such symbols, the visual charting method preserves the complexity and nuance in the content of a medical document that text-based approaches provide, while substantially reducing the amount of time it takes the practitioner to create the documentation. In essence, medical charting concepts requiring the recording of detailed information can be represented by specific images, the selection of which allowing medical documentation to be created in a more efficient manner.

The features of this invention provide a number of additional advantages, and solve problems heretofore present in the art. The images can serve as synonyms for concepts which might require detailed descriptions (in text). Visual charting can conserve space on forms and reduce the need for scrolling a form or navigating to multiple forms, further adding efficiencies to the process. The images in the visual charting approach can be converted into specific properties of class objects in an object-oriented programming environment, which can populate or be populated by a Key/Value pair relational data construct using a database or XML (extensible markup language) or other text-based representation of object properties. Visual charting further improves the ability to efficiently chart on small platforms such as Smart Phones, Pocket PCs, iPhones, iPads and similar devices. Additionally, the visual charting methods provides the ability to chart (i.e., create documentation) without a keyboard, i.e., without entering any text at all.

The invention will be described below in several different aspects. In one aspect, a method of creating a medical document using a computing device (for example a desktop workstation, smart phone, tablet computer, or the like) having a display, is described. The method includes the steps of:

(a) presenting on the display an image representing a medical concept, such as an organ or organ system of a human or animal body;

(b) enabling selection of a parameter associated with the medical concept by means of selecting a portion of the image corresponding to the parameter;

(c) responsive to the selecting in step (b), presenting on the display a set of images comprising possible values associated with selected parameter;

(d) enabling selection one of the images in the set of images presented in step (c); and (e) constructing a medical document based on the selecting in steps (b) and step (d) and storing the medical document in a computer system. The images selected in steps (b) and (d) are interchangeable with (i.e., synonyms of) a language description of the selected parameter and the selected value of the selected parameter. The selection of the parameter in step (b) may be accomplished using visual methods, such as selecting (e.g., by touch or mouse click) a portion image of medical concept image representing the parameter. Examples of this method will be described below in further detail in conjunction with visual charting of a cardiac patient, in which the image representing the medical concept is an image of the heart, the parameter selected from the image is one of the heart valves, and the selection of one of the heart valves causes display of a set of images associated with murmurs (or other possible values) of the selected heart valve.

The method can be performed iteratively in which additional parameters are selected and visual charting is used to select values for additional parameters. Thus, the method may include the repeating steps (b), (c), (d) and (e), wherein the repeated step (b) comprises the selection of a different parameter associated with the medical concept. In this manner a medical document consisting of multiple parameter/value pairs can be created.

To facilitate ease of use and understanding of the images, the method may further include the steps of displaying on the display the language textual description or synonym for each of the images selected in steps (b) and (d).

In one possible embodiment, the medical document created using the method can be saved as a text file in a predetermined format, such as an XML format. Additionally, the medical document can be saved as a Key/Value pair in a database, the Key corresponding to the selection in step (b) (either in the form of text or in the form of data representing the portion of the image selected) and the Value corresponding to the selection in step (d) (again, either as image or its textual synonym). Alternatively, the selections in step (b) and (d) can be saved as properties of a class object in a object-oriented system.

The visual charting system can be used with the charting of virtually any medical concept which lends itself to medical note writing in terms of parameter and value pairs. For example, the medical concept that is displayed can be a organ or organ system such as the heart, the circulatory system, the respiratory system, the kidneys, the digestive system, the skeletal system and the central nervous system.

In another aspect, the invention can be considered an improvement to a computing device used for medical document creation. The computing device can take the form of a desktop workstation, smart phone, tablet computer, or the like. The computing device has a display, and memory storing instructions for execution by a processing unit in the device, all of which is conventional. The improvement takes the form of a visual charting application coded as a set of instructions executed by the processing unit in the device, wherein creation of a medical document by the visual charting application is performed by selection of images or portions thereof presented on the display of the computing device, the images including images of a first type acting as a synonym for a medical parameter and images of a second type of acting as synonyms of values of the medical parameter, wherein a selection by the user of an image of the first type causing a display of a set of images of the second type to be presented on the display.

Since the images are synonyms for a textual description, the selections of the user can be saved as either textual descriptions or alternative as a set or sequence of images. For example the images can be selected as "key/value" pairs or "parameter/charted observation" pairs using concepts configured with primary keys of a relational database to achieve the same data relationships that are created when text-based language forms are used to capture information.

In still another aspect, a method of creating electronic medical documents is described using visual charting. The method includes the steps of:

(a) creating a data structure with persistent data comprising descriptive information associated with a plurality images to be presented on a medical documentation template displayed on a computing device, the images representing medical concepts such as an organ or organ system of a human or animal body;

(b) rendering one of the images in the medical documentation template on the computing device (e.g., an image of the heart);

(c) receiving a user selection on the computing device of a parameter of the medical concept by selecting a feature in the image corresponding to the parameter (e.g. selecting a portion of the heart image corresponding to one of the heart valves);

(c) responsively displaying on the display a set of images associated with values of the selected parameter (e.g. images of possible murmurs or types of murmurs of the selected heart valve);

(d) receiving a selection of one of the images in the set of images; and (e) creating a medical document reflecting the selection of the images and storing the medical document in a database.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIGS. 3-11 are a series of screen shots of a workstation, smart phone, or other computing device used by a medical practitioner showing the process of creating a medical document concerning a patient using a visual charting method.

DETAILED DESCRIPTION

Figure 1:
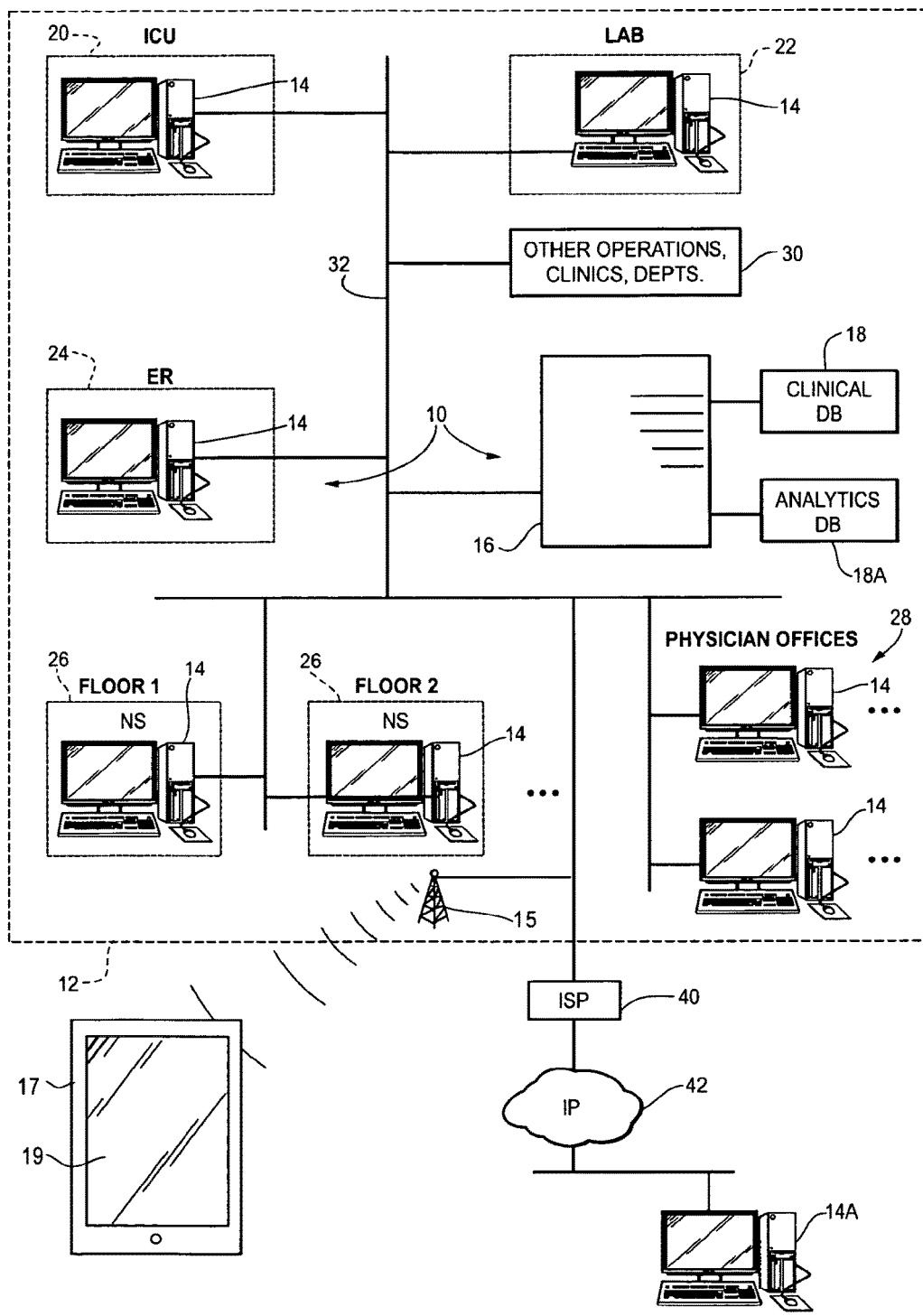
FIG. 1 is a block diagram of a computer electronic medical records system implemented in a medical facility such as a hospital.

Visual charting is a form of medical note writing that incorporates images as synonyms for Key/Value pairs. The process of visual charting results in the development of structured information for an electronic medical record that can be stored or rendered as either a "language" (i.e., textual) medical note or as an image medical note. Some of the images used in visual charting represent a description of a "key", also known as a parameter or a question regarding a medical concept (e.g., organ or organ system). Other types of images used in visual charting represent an observed finding regarding the parameter, also known as a charted observation or a value or an answer. Together, the images of both the parameter and the value represent unique combinations within the electronic medical record, commonly known as key/value pairs.

The result of the visual charting method is the creation of a medical document, which may take the form of a textual note, as well as the storage of key/value pairs within the database (e.g., in an electronic medical record). The result can also be stored or represented in other forms, such as an XML (extensible markup language) document representing the information. The concept of visual image synonyms representing the definition keys of structured note writing make the images interchangeable with a textual description of the concept captured or conveyed by the image selected. Alternatively, the result of visual charting can be saved as properties of a class object in a object-oriented system.

The visual charting methods of this disclosure will be described in detail later in this document in conjunction with FIGS. 2A-11. In brief, the methods involve presenting on the display of a computing device an image representing a medical concept, such as an organ or organ system of a human or animal body. From that image, a body part or sub-region of the image is selected which represents selection of a parameter or set of parameters related to the body part or region. In response to that selection, the user is presented with a display of a set of images comprising possible values associated with selected parameter. In other words, the user is presented with multiple images that can be selected to describe the appearance, or the physical exam or verbal answers to questions related to the body part or region, i.e., values associated with the selected parameter. A medical document is then constructed based on the selections of the parameter and values, and the medical document is stored in a computer system. For example, as the user selects the images during visual charting, the computer system is building an XML representation of the textual synonyms of the selected images. The medical document can be represented in other equivalent manners, such as a textual representation of the questions and answers associated with the images, or as a class object properties and values representing a structured or non-structured set of key/value pairs or question/answer pairs.

A description of one possible hardware and software environment in which the invention can be practiced will be described next. In the following section an example of visual charting will be provided.

A. Hardware and Software Environment of Invention

Referring now to FIG. 1, a representative and non-limiting example of an environment in which visual charting can be practiced is shown in block diagram format. In particular, FIG. 1 depicts a computerized medical records system 10 that is used by clinicians (physicians, nurses and other medical personnel) and hospital administration staff. The system is shown installed in a medical facility 12 indicated in dashed lines. The medical facility may for example be a hospital, nursing home, clinic, or other medical enterprise. The details on the medical enterprise and type of health care services it may render to patients are not particularly important. One possible application of this invention is in the hospital environment, and therefore the following description will be made in conjunction with a hospital, but again this is only by way of non-limiting example.

The medical records system 10 includes a plurality of distributed computing devices or workstations, e.g., client computers 14, a central database server 16, and a database 18 storing, among other things electronic patient records including medical documentation created using the visual charting methods of this disclosure. Clinical data can be extracted from the database 18 and loaded into an analytics database 18A for data analysis and reporting in the manner described in US Patent Application Publication No. 2009/0024414. The workstations 14 could be for example general purpose computers with a processing unit and graphical display unit and mouse or other pointing device for section of images using the methods of this disclosure. The workstations 14 could also be portable computing devices such as hand-held computer, smart phone or tablet PC shown at 17 having a display 19 in the lower left of FIG. 1. The portable computing device communicates with the network 32 via a wireless base station 15 using a suitable and known telecommunication methods (e.g., Bluetooth, WiMax or cellular telephone network). The workstations 14 include a memory storing an interactive, client-server based patient documentation application that is executed by the processor in the workstation. The application provides user interface tools in the form of graphical screen displays which allow the user access the electronic patient records stored in the database and create clinical documentation regarding a patient being treated at the facility 12 using the visual charting methods described in FIGS. 2A-12.

As shown in FIG. 1, the facility 12 may include an Intensive Care Unit 20 with a workstation 14, which may be used by ICU physicians and ICU nurses to access patient records and input orders, write prescriptions, view patient allergies, and create medical documentation. The facility may also include one or more laboratories 22, each of which may include a workstation. Lab personnel may input test results into the patient record stored in the database 18. The facility may also include an Emergency Room (ER) 24, where a workstation 14 is provided for ER clinicians to records and input orders, write prescriptions, view patient allergies, note significant events and chief complaints, etc. of the patients and input them into the electronic patient record stored in the database 18. The facility may also have a number of patient rooms and provide nurses stations (NS) 26 on each floor, each of which has a workstation 14. Additionally, physicians' offices 28 may also include workstations 14, in the form of personal computers. The facility 12 may have other operations, clinics, departments, etc. as indicated at 30, each of which may be provided with additional workstations. The workstation are networked on a local area network 32 wherein all of the workstations may exchange data with the central database server 16 and thereby access the patient records stored in the database 18 and write documentation and orders, prescriptions, and other information to the database 18.

The network 32 may include a router (not shown) providing a connection to an internet service provider (ISP) 40 providing access to an external wide area internet protocol network 42 such as the Internet 42. A workstation 14A may be coupled to the enterprise network 32 via the ISP 40 whereby a clinician authorized to access patient records in the database 12 may do so via the Internet 42, ISP 40 network access server and local area network 32. Thus, a workstation 14, 14A creating patient documentation need not necessarily physically reside on the network 32 or be physically located within or at the enterprise 12.

The medical records system 10 allows clinicians to create new medical documentation and store such documentation in the database 18, as well as access patient records in a clinical database 18. The system 10 may take the form of a hospital medical records information system, and such systems are generally known in the art and commercially available from Allscripts Health Care Solutions, Inc., and others. The preferred embodiment of such a system provides clinicians information they need, when and where they need it—at the point of care, e.g., in the ER or at the nursing stations 26, in the offices 28, via Smart Phones or portable PCs 17, and even at home via a computer 14A and the Internet 42.

Figure 2:
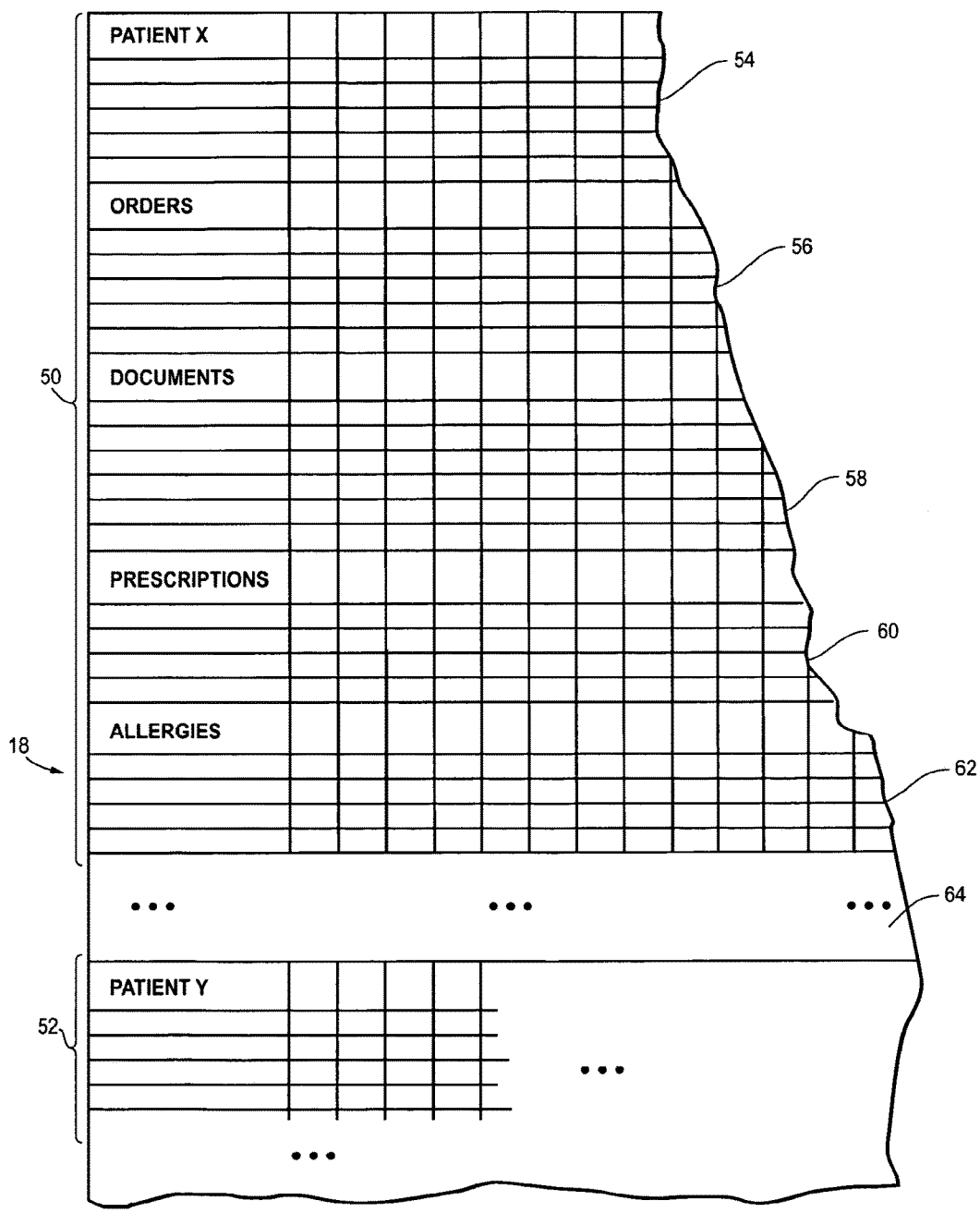
FIG. 2 is a schematic representation of a portion of the clinical database of FIG. 1, showing an electronic patient record for patient X, with the record including a number of fields or categories, each associated with a different portion of the database record. These categories, which may be user or customer defined, include categories such as Orders, Documents, Prescriptions, Allergies and still others. The illustration of FIG. 1 shows a relational database implementation wherein data is organized in rows and columns. However, the use of object-oriented database design in which data is stored as objects is an alternative implementation.

A schematic representation of the database 18 is shown in FIG. 2. The database includes a multitude of electronic patient records 50, 52 each comprising rows and columns of data. A first field 54 is shown directed to patient information, such as name, address, insurance carrier, date of birth, etc.

A second field 56 contains orders for the patient. The orders are determined by health care personnel treating the patient. Each row in the orders field 56 may constitute a specific order, and the various columns in the row devoted to different aspects of the order, such as the entering physician's name, the type of order, the date it was placed, etc.

A third field 58 is directed to documents (i.e., medical documentation) entered by a physician or nurse. Each row may represent specific instances of documentation created by a user.

A fourth field 60 contains prescription medications ordered for the patient. A fifth field 62 contains data of all the patient's allergies. Other fields 64 are also present, and may include fields devoted to significant events, health issues, care providers and others. The name of the categories in the electronic patient record, and the number of categories is not particularly important and may vary depending on the environment and the choices made by a system administrator.

B. Visual Charting Example

Visual Charting represents the development of medical charting tools that incorporate images as synonyms for interchangeable values in Key/Value pairs in a data structure or properties of class objects representing medical concepts, such as a description of a cardiac examination or any other body area or organ system. The image of the anatomic representation of the organ or the finding related to the organ system correlate to a primary Key in an electronic medical record to represent the concepts. The concepts represented by the images are interchangeable with the language descriptions of the same concept such that the concepts could be represented in a medical note as the image or the language description. The persistent data representing the medical note could be held in a database in FIG. 2 in a variety of forms, for example a text based representation of a data such as XML.

When computing with these forms and collecting the medical data the organ systems and descriptions are represented as class objects with properties (or XML) that can be populated by the medical worker through a forms system, an electronic medical record database or a text based data structure such as XML. The medical charting tool can be defaulted to normal images representing "normal status" in medical language. The medical language is interchangeable with the images and is represented by unique keys which could be defined in a proprietary language or a distributed standard such as SNOMED CT. Computer code handles the definition of the class objects and the assignment of the class property values to the class objects, the reading and writing of XML, the reading and writing to the database structures and the rendering of the user interface. This technology will be used any type of computer workstation to include the smart phone, iPhone, iPad, laptop, tablet, fixed workstation of any other electronic device that is used to interact as a user interface for the electronic medical record.

Figure 2A:
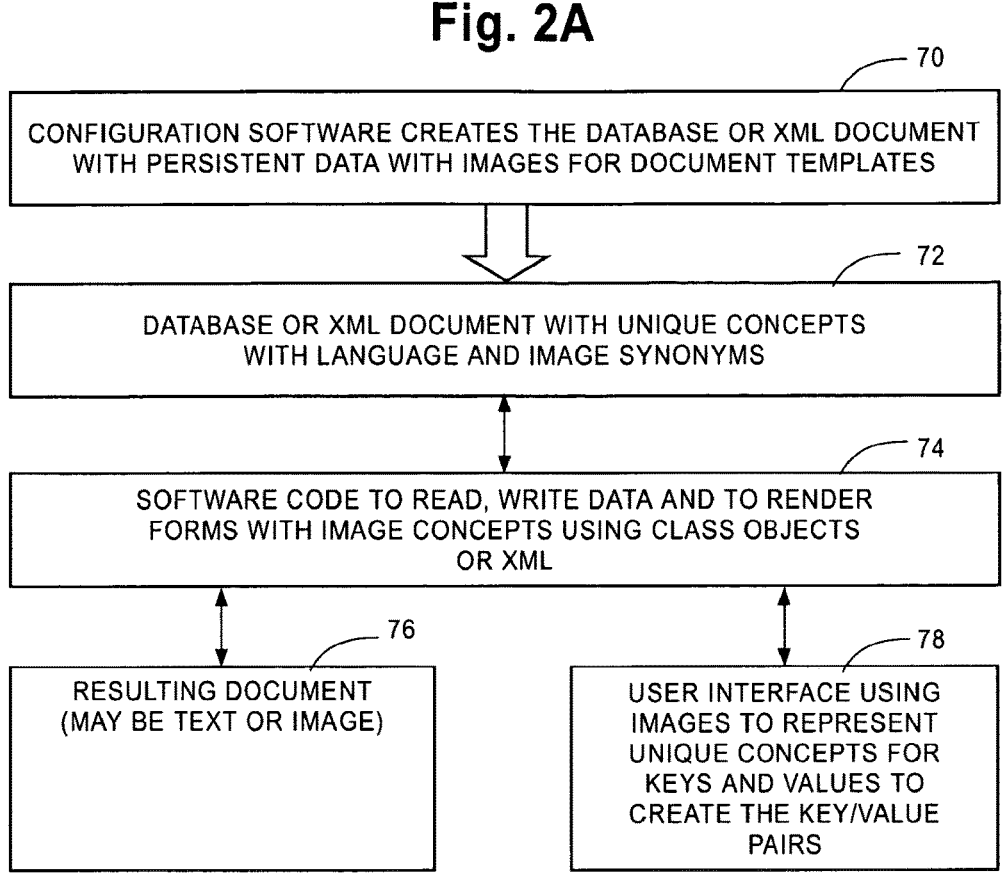
FIG. 2A is a flow chart showing a process of creating a visual charting capability in the medical records system of FIG. 1 and using it to create clinical documentation which can be stored in the database of FIG. 2.

FIG. 2A shows how a visual charting system is created and operates. In box 70, configuration software creates in the database persistent data defining images for medical documentation templates, and the textual synonyms associated with such images. The configuration software could alternatively create XML documents with such data. Such database (or XML document) is represented at 72. The system includes software code represented at 74 which reads and writes data and renders forms (document templates) on the displays of the computing device used for visual charting. Such forms include the images to represent complex medical concepts and values (charted observations) as described herein using class objects or XML, depending on the implementation. User interface software 78 resident on the computing device displays the images to represent unique concepts for Keys and Values to create Key/Value pairs, and the user interacts with this software to create medical documentation. As a result of the user interacting with the software 78 during the visual charting, resulting medical documents 76 are created and stored in the database 18 of FIG. 1, which can be in either text or image format, or in some other format.

An example of the use of visual charting will be now described in conjunction with FIGS. 3-11. The display 100 of a computing device (workstation 14, or portable computer 17 of FIG. 1) includes a text box 102 in which textual synonyms for images displayed on the display and selected by the user is set forth for the convenience of the user. The workstation includes a pointing device such as mouse or touch sensitive screen which controls a cursor 104 for making selection of images or portions of the image. In this example, the display 100 shows two views 110 and 112 of a human body and in particular the heart 108.

Figure 3:
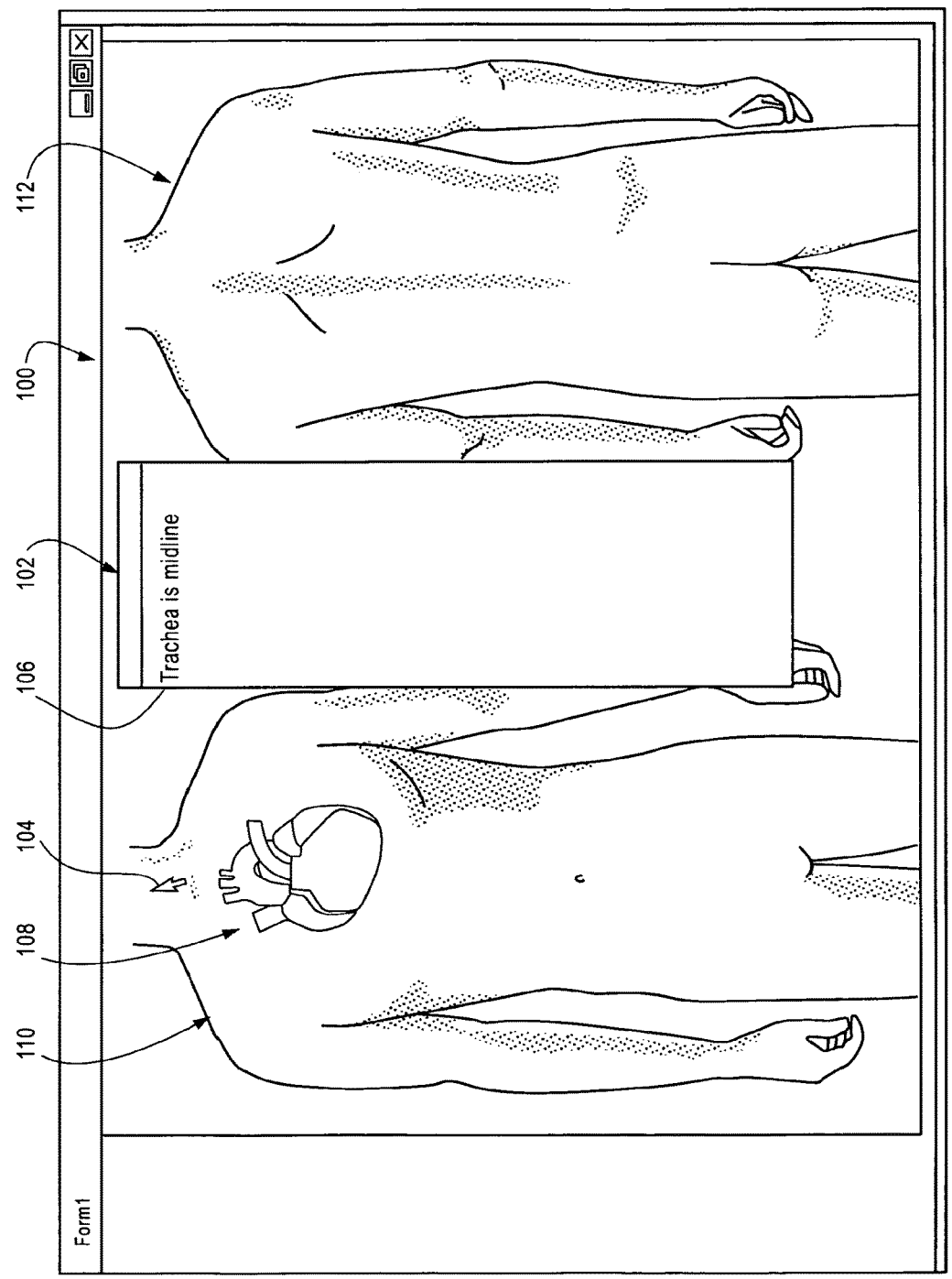

In general, the user interface of FIG. 3 displays an image or images (110, 112 108) which can be used to select a specific medical concept (key) and a specific value for the concept. In this example the user is controlling the cursor 104 to point to the trachea as part of the examination of the neck. The first click of the mouse may set the Key or Parameter as the unique concept of neck anatomic part "Trachea," which is represented with the configuration of the database as a specific parameter or observation (Key). The next click over the midline of the neck indicates the value is "is midline." The selections just described would lead to the saving of the Key/Value pair at the Class Object Property level, the XML representation level and the database level. If this note were to be recalled from the database, "Key/Value" pair could recreate the annotation through interpretation by the computer code.

In software relational database development and structured note configuration, each row has a unique identifier often referred to as the primary key. Each column of the table is an attribute of the primary key. If the primary key is related to a row in another table one of the columns will contain a pointer to that row and this is known as the foreign key.

The primary and foreign key together is a type key/value pair as are the descriptors for the rows, such as "Trachea/is midline" in the preceding example. These concepts can have an image synonym or a location on an image synonym. The interchangeable nature of the image and image location synonyms is one of the unique feature of this invention. The primary and foreign keys can both be represented with language or visual image descriptors and they are interchangeable.

Figure 4:
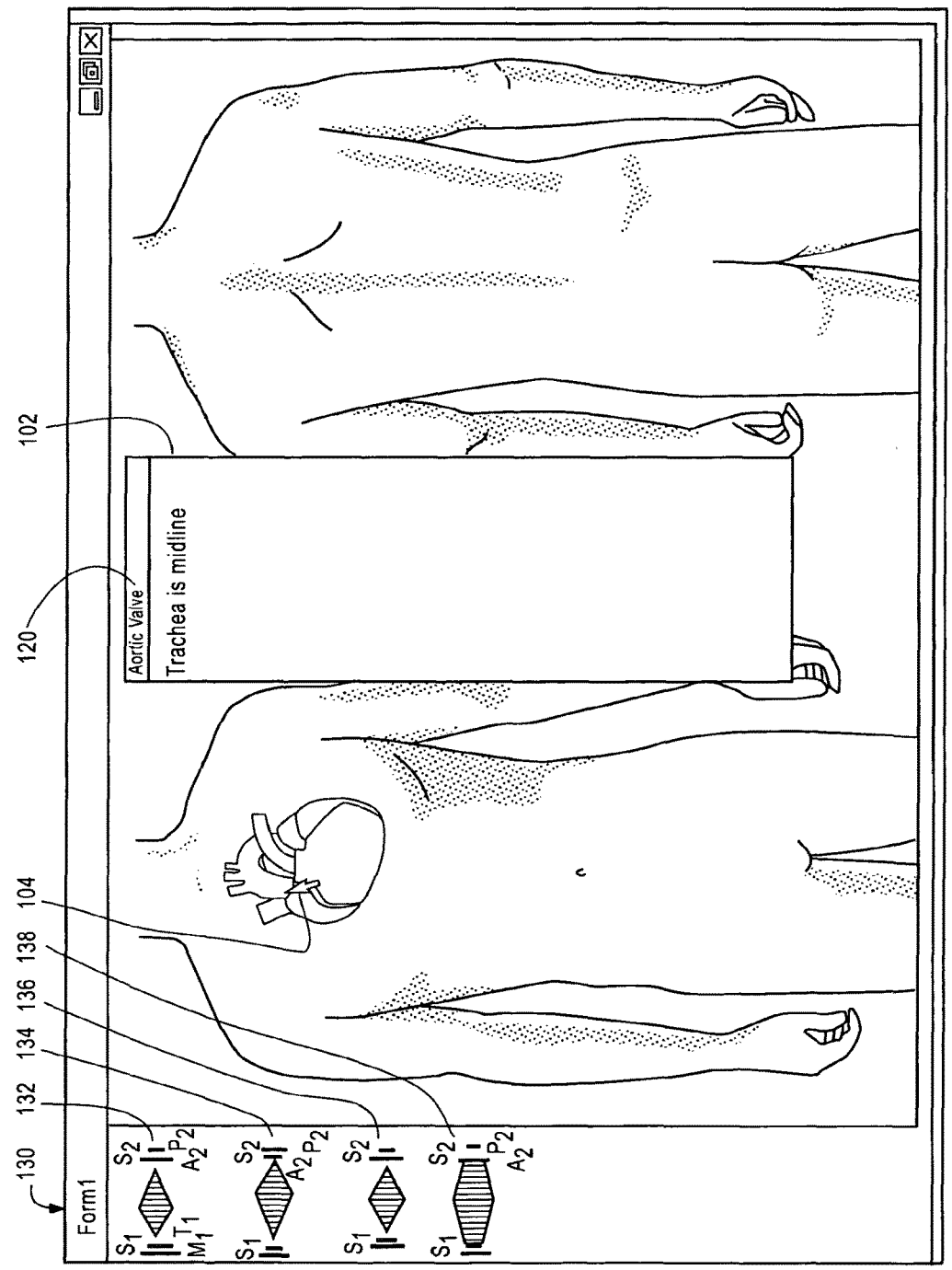
Figure 5:
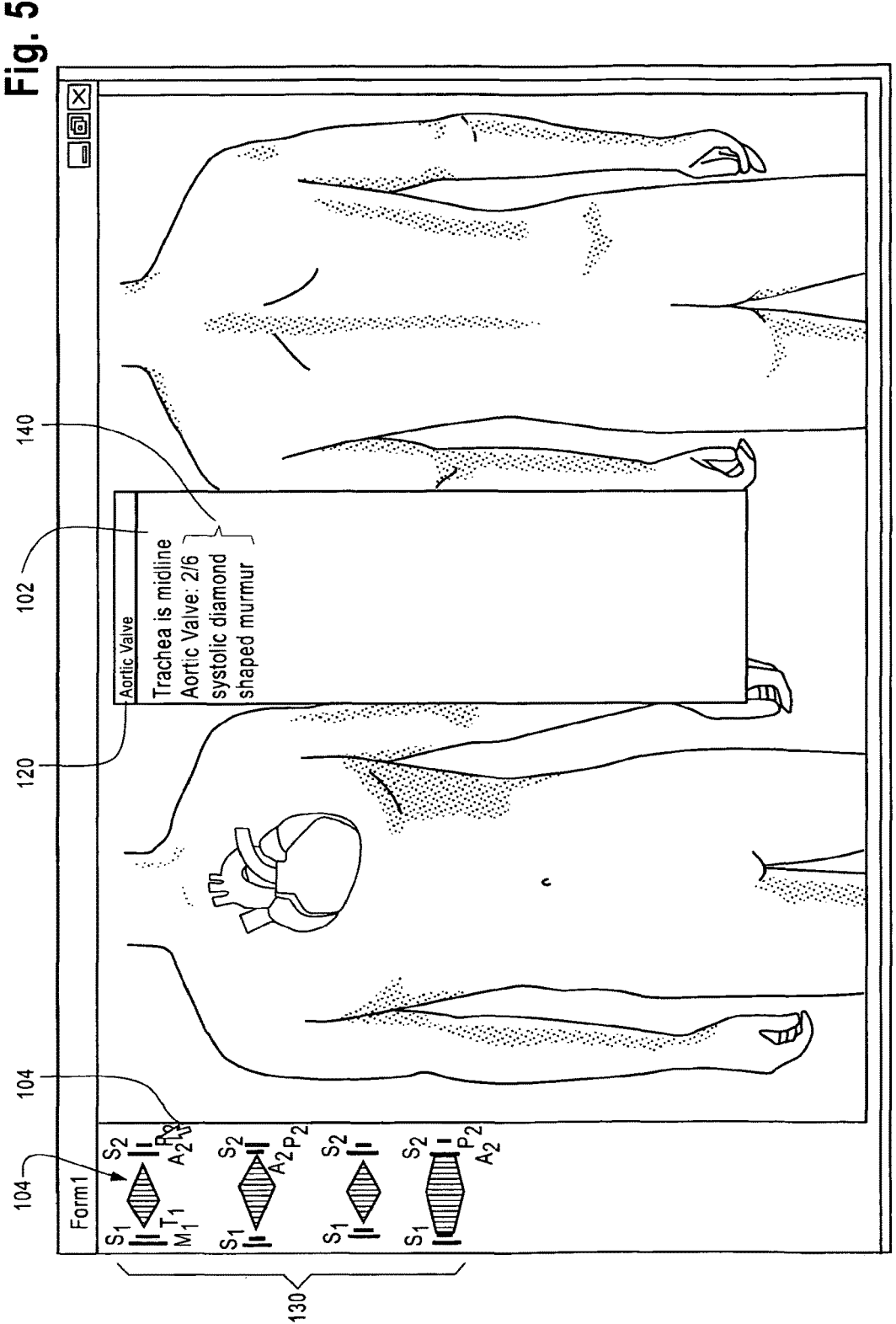

Another example of selection of a Parameter/Key and Value/Charted Observation is shown in FIG. 4. In this example, the medical concept shown in the image is the Heart. The user moves the cursor over the aortic valve area of the image and selects a portion of the image, in this example selects the key of "aortic valve auscultation" or simply "aortic valve." In response, the text "aortic valve" appears in the window 120 of the text box 102 indicating this selection. Furthermore, selection of the parameter "aortic valve" causes a set of images 130 on the left hand side of the display to be presented. These images 130 provide a menu of possible values or charted observations for the selected parameter/key "aortic valve", and in this example the images 132, 134, 136 and 138 represent different types of murmurs. Referring to FIG. 5, the first image 132 in the set or series 130 is selected as indicated by the cursor position 104 by clicking, and then language description shown at 140 is written to the form. The language description correlates with the database row associated with the selected parameter Aortic Valve. The database row contains a unique identifier for image 132, for example a textual description for a systolic crescendo/decrescendo murmur that begins shortly after the first heart sound (closure of the mitral and tricuspid valves), reaches a peak in volume just after mid-systole (ejection of the blood from the left ventricle into the aorta) and tapers off in late systole before the second heart sound (closure of the aortic and pulmonary valves). This image 132 demonstrates a pathologic condition of the aortic valve. This example demonstrates the extraordinary efficiency of a small image (132) to convey and very large and complex physiologic concept, and the simple act of selecting such an image shortening the time needed to enter associated information into a medical document. Instead of the physician having to type this concept (or dictate it), the physician can simply select the image and move on to recording other observations regarding the patient.

Just as the images 130 come from a finite selection of abnormal findings, the language descriptions of these abnormalities are also finite in number and have a one to one correlation with the images. Therefore, the image and its language descriptor relate to a unique compound concept represented by a Key/Value pair.

The Key of a Key/Value pair (such as the Aortic Valve in FIGS. 4 and 5 or the Trachea in FIG. 3) will have different values depending on the patient answers or clinician observations.

On the charting forms (such as for example the charting form or template shown in FIGS. 3-5) the keys are represented by images or portions thereof, as are the values. In one example, selecting an image (or portion thereof) to indicate selection of a key, such as the Trachea, or Aortic Valve, causes the appearance of one or more selectable images (130). Selecting an image in the set of images 130 creates one key/value pair, e.g., Aortic Valve/systolic diamond shaped murmur in the example of FIG. 5.

Figure 6:
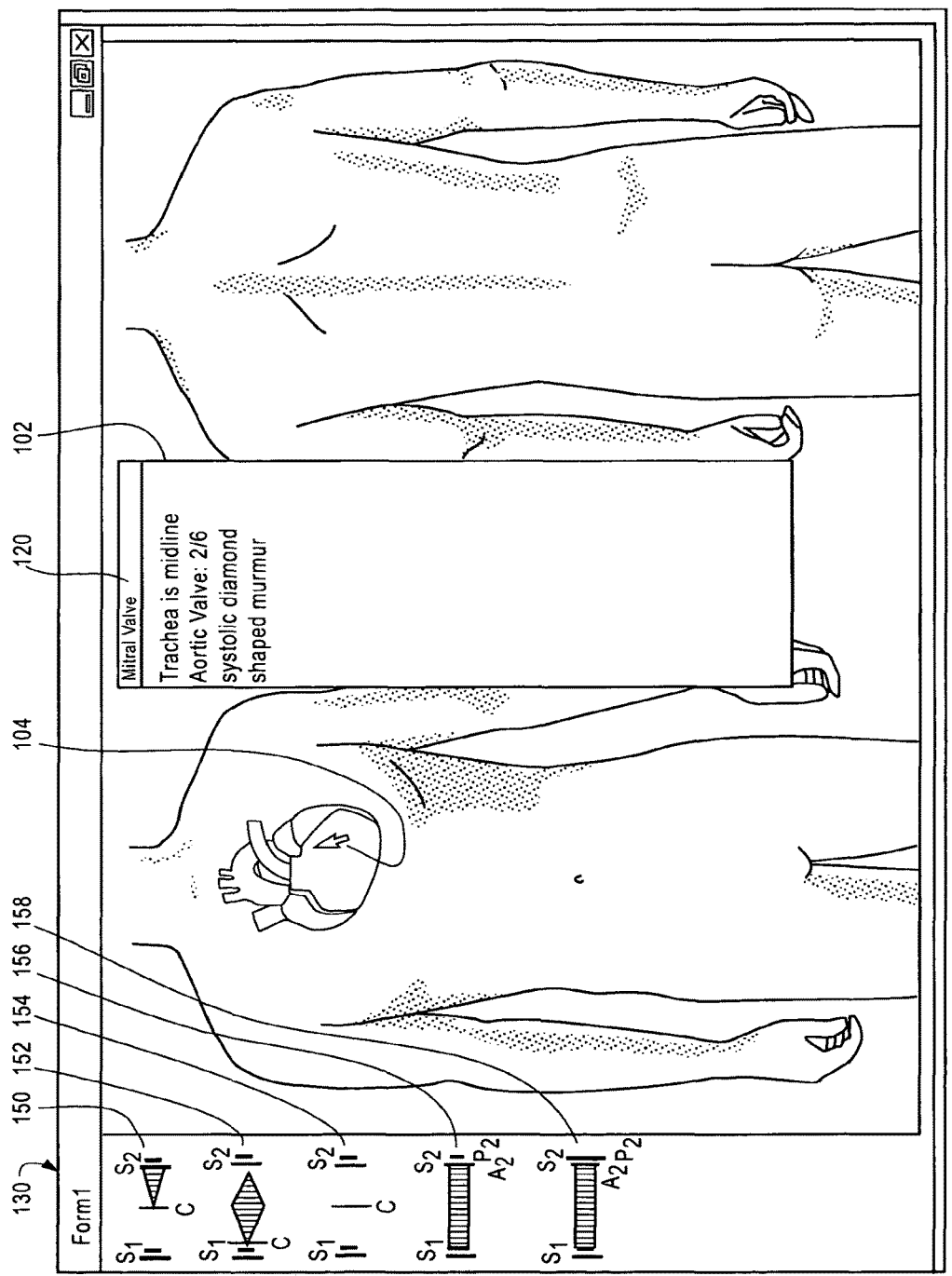
Figure 7:
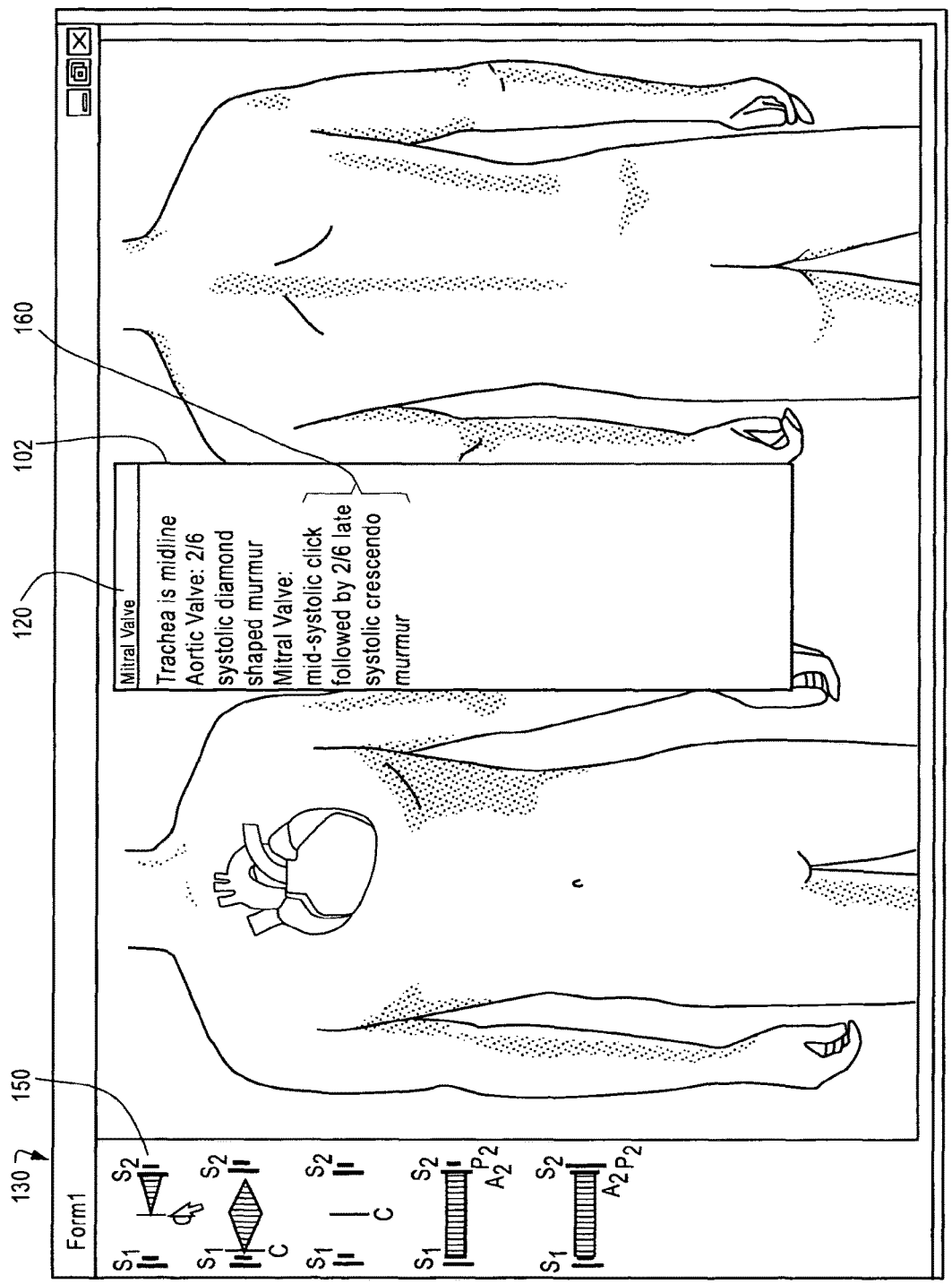

A structured medical note is typically made of many key/value pairs. An example of how a structured medical note consisting of many key/value pairs is constructed will be demonstrated in FIG. 6 and the following figures. In essence, the selection of parameters/keys and values as described above is repeated as many times as deemed necessary by the user in order to complete the creation of the note. For example, after the selection of the value (image 132) for the aortic valve parameter, the user moves the cursor 104 to another area of the heart as shown in FIG. 6. In this example the user holds the cursor over the mitral valve area of the heart and clicks the mouse or otherwise selects that portion of the image. The text box 102 now displays "mitral valve", indicating the selection of mitral valve as the key/parameter. In response, a new set of images 130 is displayed on the display, each one of the images 150, 152, 154, 156, 158 associated with a different murmur or observation ("Value") associated with the mitral valve. In this example, and with reference to FIG. 7, the user selected the image 150. This image is a synonym for a text-based representation of a particular mitral valve murmur, in this example a mid-systolic click followed by a 2/6 late systolic crescendo murmur. The selection of image causes the additional text shown at 160 to be added to the medical note. (Depending on space constraints and the user interface design, the text shown in the text box 102 may be a complete rendering of the textual synonym associated with the selected image 150, or it may be a shorthand or abbreviation of that textual synonym. In the case of an abbreviation, the display may include a feature by which the user can see displayed the entire text corresponding to the image, such as a link or an icon which when selected causes a window to pop up that displays the entire text).

Figure 8:
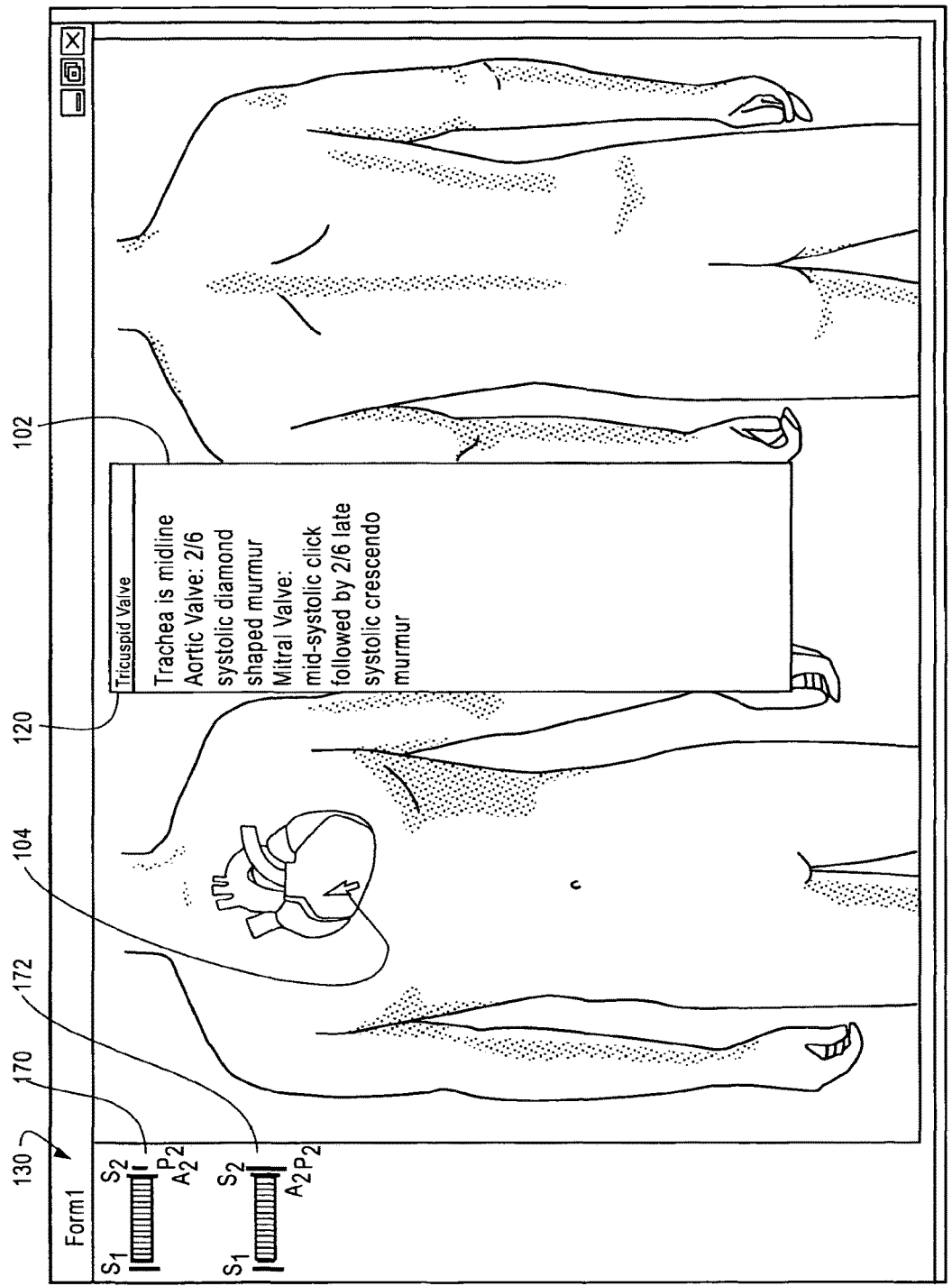
Figure 9:
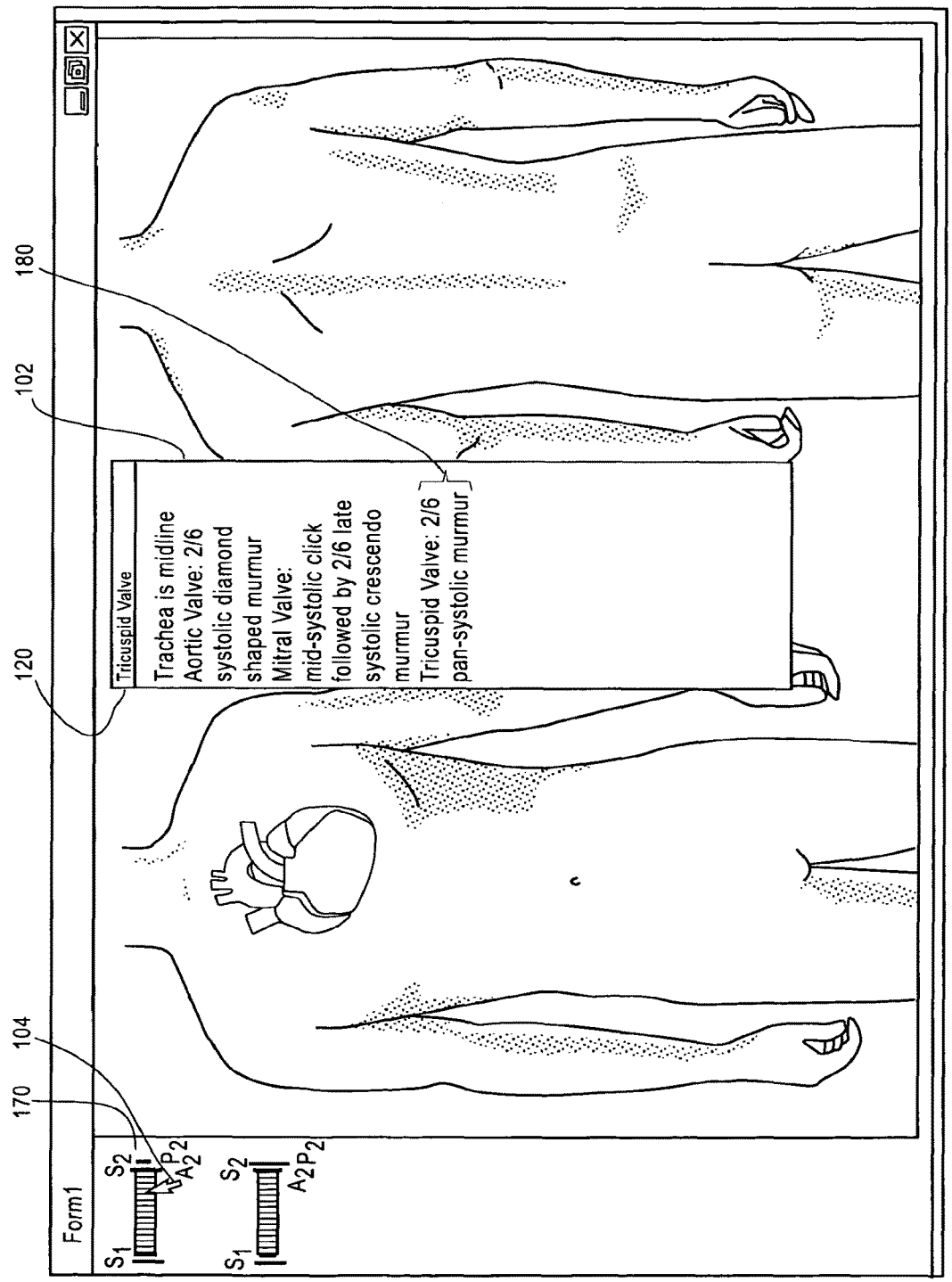

Continuing on with FIG. 8, the user has now moved the cursor over the triscuspid valve area of the heart and clicked the mouse, thereby indicating selection of the tricuspid valve as the next Key in a Key/Value pair. The selection of the tricuspid valve causes the text "tricuspid valve" to appear in the window 120, confirming the selection to the user. At this point, two new images appear in the area 130 representing potential Values for this Key. The images 170 and 172 represent two murmur types associated with the tricuspid valve. Referring to FIG. 9, the user moves the cursor over to the image 170 and clicks it to indicate selection. The text associated with the image 170 now appears in the text box 102.

Figure 10:
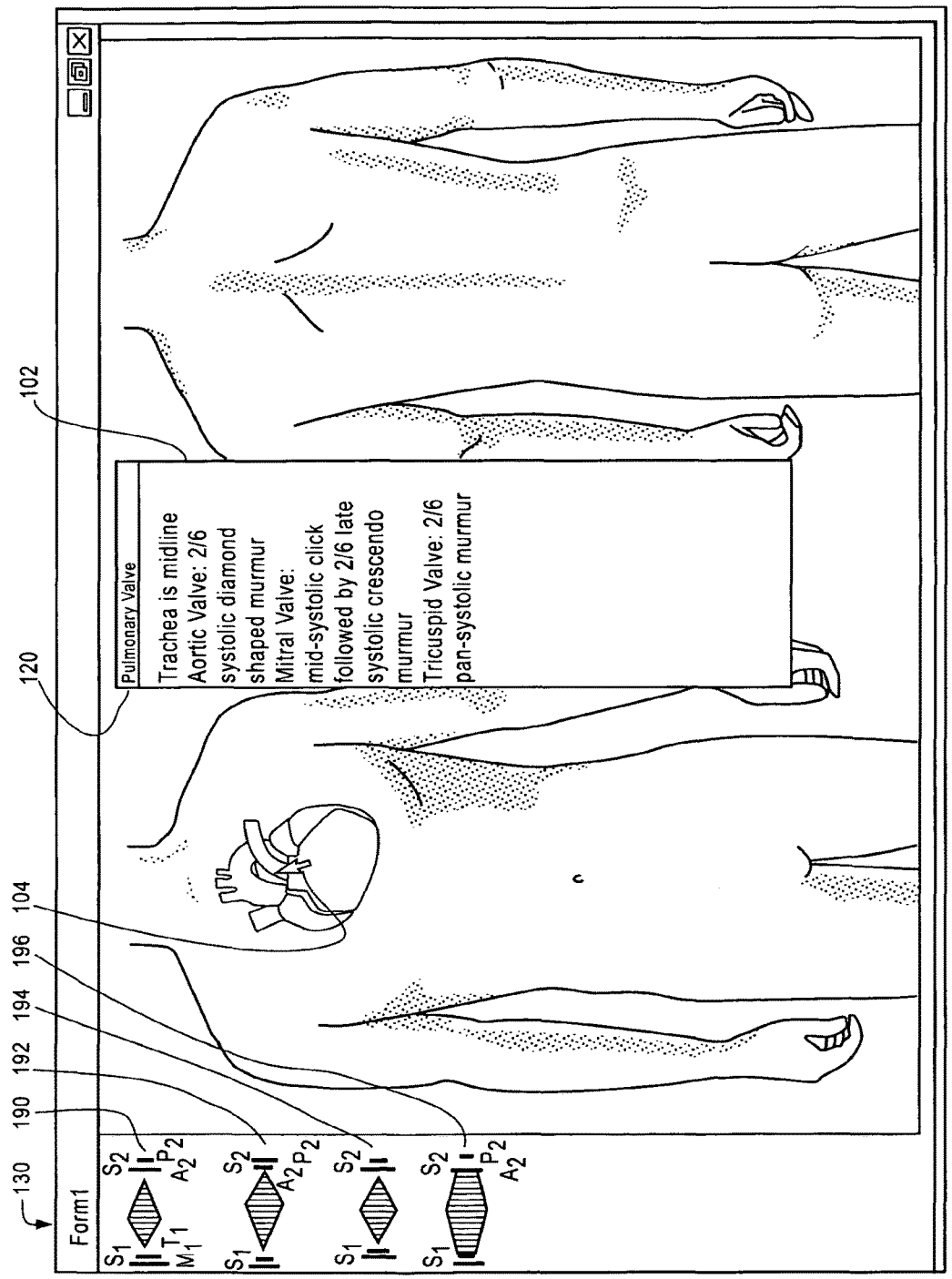

Referring now to FIG. 10, the user has proceeded to move the cursor 104 over to the pulmonary valve portion of the heart image and selected it by clicking the mouse. The text "pulmonary valve" now appears in the window 120. The selection of this Parameter/Key causes a new set of images 190, 192, 194 and 196 to be displayed, each one associated with different potential values for the selected parameter "pulmonary valve." Referring to FIG. 11, the user selects image 190 by moving the cursor 104 to the location of the image and clicking the mouse, which causes the textual description 200 associated with image 190 to appear in the text box 102 ("2/6 systolic diamond shaped murmur").

The process described above can of course continue further, by the user selecting additional portions of the image of the body or the heart to signify selection of different parameters and then selecting one of the images associated with different values for the selected parameter. Additional tools for going back, saving, editing, selection of different organ systems, and so on are not shown but can of course be part of the user interface design, and these details are considered within the ability of persons skilled in the art.

In the software code, in one possible embodiment the key/value pairs are represented as class objects, class members, properties and property values. More than one class object may be defined as part of the coding process. If a note has been started and saved but not finalized, the note may be opened in an edit mode, in which case the software code will read the key/value pairs from the database or XML document containing the key/value pairs selected in a prior session, populate the class objects and property values or XML, and render the form with the image representation of the saved data.

In some cases, visual charting of key/value pairs will be used to display text when the document is rendered to the user. In other cases, the key/value pairs can be used to render charted values displayed or superimposed on images. A unique feature the invention is the interchangeability of the image synonyms and specific image locations with the language descriptors of the specific concepts.

The recorded, saved and persisted data can be stored in a database, or as a text file with a specific format such as XML. The computer code can be written in any language capable of rendering a form, reading and writing to a database and reading or writing to XML or other formatted text file and creating an object or object like structure in which member and properties can be assigned values, methods can be created and object state can be loaded from a persistent data representation or unloaded to a persistent data representation. An example of such code is set forth below:

TABLE-US-00001 Object Oriented Class Class Physical_ Exam Private Cardiac_S1 as string Private Cardiac_S2 as string Private Cardiac_S3 as string Private Cardiac_S4 as string Private Cardiac_Aortic_Value as string Private Cardiac_Mitral_Value as string Private Cardiac_Tricuspid_ Value as string Private Cardiac_Pulmonary_Value as string Public Property pCardiac_S1 as String Get RETURN Cardiac_S1 End Get Set (ByVal value As String) Cardiac_S1=value End Set . . . End Class There are many potential commercial use(s) for the invention: Hospital Clinician Charting; Medical Office Clinician Charting; Long-term care facility Clinician Charting; Nursing Home Clinician Charting; Rehabilitation facility Clinician Charting; and Clinician Charting on Mobile User Interface Platforms, including smart phones, iPhones, iPads, Pocket PCs, or any other mobile device used for medical charting. Additionally, the computer device used for medical charting can include laptop computers, tablet computers and fixed workstations. The invention is suitable for touch screen user interface systems. In general, any computing device having a processing unit, a memory storing software computer instructions and a user interface adapted for medical charting against an electronic medical record can be used.

In view of the above description, it will be appreciated that a method of creating a medical document using a computing device (14/17) having a display using visual charting has been described, comprising the steps of:

(a) presenting on the display (FIG. 4) an image representing a medical concept, such as an organ or organ system of a human or animal body (e.g., the heart in FIG. 4);

(b) enabling selection of a parameter associated with the medical concept by selecting a portion of the image corresponding to the parameter (e.g., selection of the parameter "aortic valve" in FIG. 4);

(c) responsive to the selecting in step (b), presenting on the display a set of images (130, FIG. 4) comprising possible values associated with selected parameter;

(d) enabling selection one of the images in the set of images presented in step (c) (selection occurring by clicking the cursor while the cursor is over the image as shown in FIG. 5, or by means of touching the image in a touch sensitive display embodiment); and (e) constructing a medical document based on the selecting in steps (b) and step (d) (see FIG. 4, text box 102) and storing the medical document in a computer system (FIG. 1, e.g., in the database 18) wherein the images selected in steps (b) and (d) are interchangeable with a language description of the selected parameter and the selected value of the selected parameter.

It will further be appreciated from the foregoing description that a new and improved computing device for visual charting has been described. The computing device (FIG. 1, 14, or 17) has a display (FIG. 4), and memory, not shown but conventional) storing instructions for execution by a processing unit (not shown, but conventional) in the device. The improvement takes the form of a visual charting application coded as a set of instructions executed by the device, described by way of example in FIGS. 4-11), wherein creation of a medical document by the visual charting application is performed by selection of images presented on the display of the computing device, the images including images of a first type acting as a synonym for a medical parameter (e.g., the image of the heart or a portion thereof corresponding to a particular valve) and images of a second type (images 130 in FIGS. 4-11) acting as synonyms of values of the medical parameter, wherein a selection by the user of an image of the first type (selection of aortic valve in FIG. 4) causing a display of a set of images of the second type to be presented on the display (FIG. 4, images 132, 134, 136 and 138).

In still another aspect, a method of creating electronic medical documents has been described comprising the steps of:

creating a data structure (e.g., XML document) with persistent data comprising descriptive information associated with a plurality images to be presented on a medical documentation template displayed on a computing device, the images representing medical concepts such as an organ or organ system of a human or animal body;

rendering one of the images in the medical documentation template on the computing device (FIG. 4);

receiving a user selection on the computing device of a parameter of the medical concept by selecting a feature in the image corresponding to the parameter (FIG. 4, selection of "aortic valve" feature of the heart image);

responsively displaying on the display a set of images associated with values of the selected parameter (display of images 132, 134, 136, 138, FIG. 4);

receiving a selection of one of the images in the set of images (FIG. 5, clicking on the image 132); and creating a medical document reflecting the selection of the images and storing the medical document in a database (FIG. 1, 18).

While a number of exemplary aspects and embodiments have been discussed above, those of skill in the art will recognize that various modifications, permutations, and additions are possible. It is therefore intended that the following appended claims and claims hereafter introduced are interpreted to include all such modifications, permutations, additions and sub-combinations as are within their true spirit and scope.

What is claimed is:

1. A method of specifying and saving medical information pertaining to a patient in an electronic medical record in a medical healthcare computer system in which patient medical records are stored and updated, comprising the steps of:
   (a) first,
      (i) presenting on a touch sensitive display of a handheld wireless computing device, for view by a user, a first anatomical image representing at least a portion of a human body;
      (ii) receiving, on the handheld wireless computing device, first user input corresponding to touching by the user on the display of a first area of the first anatomical image representing a selection by the user of a first body part of the first anatomical image presented on the display;
      (iii) determining, based on the received first user input corresponding to selection by the user of a first body part of the first anatomical image, a first set of pictorial images associated with the selected first body part that are
      each symbolic of a different value associated with the first body part, wherein a combination of
         (A) the first body part of the first anatomical image of the human body selected by the user, and
         (B) one of the pictorial images of the first set of pictorial images symbolic of different values associated with the body part,
      uniquely represents a predefined textual description of medical information;
      (iv) responsive to receiving the first user input, presenting on the display of the handheld wireless computing device, for view by the user,
         (i) a text descriptor corresponding to the first body part, and
         (ii) the determined first set of pictorial images,
      (v) receiving, on the handheld wireless computing device, second user input corresponding to touching by the user on the display of an area representing a selection by the user of one of the presented pictorial images in the first set of pictorial images,
      whereby a first predefined textual description of medical information is specified by the user pertaining to the patient without typing by the user; and
   (b) presenting, on the display of the handheld wireless computing device, for view by the user, the first predefined textual description of medical information;
   (c) thereafter,
      (i) receiving, on the handheld wireless computing device, third user input corresponding to touching by the user on the display of a second area of the first anatomical image representing a selection by the user of a second body part of the first anatomical image presented on the display;
      (ii) determining, based on the received third user input corresponding to selection by the user of a second body part of the first anatomical image, a second set of pictorial images associated with the selected second body part that are each symbolic of a different value associated with the second body part, the second set of pictorial images being different than the first set of pictorial images, wherein a combination of
         (A) the second body part of the first anatomical image of the human body selected by the user, and
         (B) one of the pictorial images of the second set of pictorial images symbolic of different values associated with the body part,
      uniquely represents a predefined textual description of medical information;
      (iii) responsive to receiving the third user input, presenting on the display of the handheld wireless computing device, for view by the user, the determined second set of pictorial images;
      (v) receiving, on the handheld wireless computing device, user input corresponding to touching by the user on the display of an area representing a selection by the user of one of the presented pictorial images in the second set of pictorial images,
      whereby a second predefined textual description of medical information is specified by the user pertaining to the patient without typing by the user; and
   (d) presenting, on the display of the handheld wireless computing device, for view by the user, the second predefined textual description of medical information;
   (e) electronically communicating, from the handheld wireless computing device, to a server in the medical healthcare computer system in which patient medical records are stored and updated for storing in association with an electronic medical record of the patient,
      (i) data associated with the first and second user input as a first key-value pair corresponding to the first predefined textual description, and
      (ii) data associated with the second and third user input as a second key-value pair corresponding to the second predefined textual description.

2. The method of claim 1, further comprising creating a medical document that is stored in association with an electronic medical record of the patient, the medical document comprising the data representing the specified predefined textual description of medical information pertaining to the patient.

3. The method of claim 1, further comprising updating a medical document that is stored in association with an electronic medical record of the patient, the medical document comprising the data representing the specified predefined textual description of medical information pertaining to the patient.

4. The method of claim 1, further comprising the step of saving the medical information pertaining to the patient that is specified by the user as a text file in a predetermined format.

5. The method of claim 4, wherein the predetermined format comprises an XML format, and wherein the data that is electronically communicated from the handheld wireless computing device to the server comprises the XML data.

6. The method of claim 1, wherein the medical information pertaining to the patient that is specified by the user is saved as a Key/Value pair in a database, the Key corresponding to the selection in step (A)(ii) and the Value corresponding to the selection in step (A)(v).

7. The method of claim 1, wherein the selections in step (A)(ii) and (A)(v) are saved as properties of a class object in an object-oriented system.

8. The method of claim 1, wherein the anatomical image comprises an organ or organ system selected from the group of organs and organ systems consisting of the heart, the circulatory system, the respiratory system, the kidneys, the digestive system, the skeletal system and the central nervous system.

9. The method of claim 1, wherein the data is electronically communicated wirelessly from the computing device, over a cellular network, to the server.

10. The method of claim 1, wherein the data is electronically communicated from the computing device, over the Internet, to the server.

11. A method of specifying and saving medical information pertaining to a patient in an electronic medical record in a medical healthcare computer system in which patient medical records are stored and updated, comprising the steps of:
   (a) first,
      (i) presenting on a touch sensitive display of a handheld wireless computing device, for view by a user, a first anatomical image representing at least a portion of a human body;
      (ii) receiving, on the handheld wireless computing device, first user input corresponding to touching by the user on the display of a first area of the first anatomical image representing a selection by the user of a first body part of the first anatomical image presented on the display;
      (iii) determining, based on the received first user input corresponding to selection by the user of a first body part of the first anatomical image, a first set of pictorial images associated with the selected first body part that are each symbolic of a different value associated with the first body part, wherein a combination of
         (A) the first body part of the first anatomical image of the human body selected by the user, and
         (B) one of the pictorial images of the first set of pictorial images symbolic of different values associated with the body part,
         uniquely represents a predefined textual description of medical information;
      (iv) responsive to receiving the first user input, presenting on the display of the handheld wireless computing device, for view by the user,
         (i) a text descriptor corresponding to the first body part, and
         (ii) the determined first set of pictorial images,
      (v) receiving, on the handheld wireless computing device, second user input corresponding to touching by the user on the display of an area representing a selection by the user of one of the presented pictorial images in the first set of pictorial images,
      whereby a first predefined textual description of medical information is specified by the user pertaining to the patient without typing by the user; and
   (b) thereafter,
      (i) receiving, on the handheld wireless computing device, third user input corresponding to touching by the user on the display of a second area of the first anatomical image representing a selection by the user of a second body part of the first anatomical image presented on the display;
      (ii) determining, based on the received third user input corresponding to selection by the user of a second body part of the first anatomical image, a second set of pictorial images associated with the selected second body part that are each symbolic of a different value associated with the second body part, the second set of pictorial images being different than the first set of pictorial images, wherein a combination of
         (A) the second body part of the first anatomical image of the human body selected by the user, and
         (B) one of the pictorial images of the second set of pictorial images symbolic of different values associated with the body part,
         uniquely represents a predefined textual description of medical information;
      (iii) responsive to receiving the third user input, presenting on the display of the handheld wireless computing device, for view by the user, the determined second set of pictorial images;
      (iv) receiving, on the handheld wireless computing device, user input corresponding to touching by the user on the display of an area representing a selection by the user of one of the presented pictorial images in the second set of pictorial images,
      whereby a second predefined textual description of medical information is specified by the user pertaining to the patient without typing by the user; and
   (c) electronically communicating, from the handheld wireless computing device, to a server in the medical healthcare computer system in which patient medical records are stored and updated for storing in association with an electronic medical record of the patient,
      (i) data associated with the first and second user input as a first key-value pair corresponding to the first predefined textual description, and
      (ii) data associated with the second and third user input as a second key-value pair corresponding to the second predefined textual description.

12. The method of claim 11, further comprising creating a medical document that is stored in association with an electronic medical record of the patient, the medical document comprising the data representing the specified predefined textual description of medical information pertaining to the patient.

13. The method of claim 11, further comprising updating a medical document that is stored in association with an electronic medical record of the patient, the medical document comprising the data representing the specified predefined textual description of medical information pertaining to the patient.

14. The method of claim 11, further comprising the step of saving the medical information pertaining to the patient that is specified by the user as a text file in a predetermined format.

15. The method of claim 14, wherein the predetermined format comprises an XML format, and wherein the data that is electronically communicated from the handheld wireless computing device to the server comprises the XML data.

16. The method of claim 11, wherein the medical information pertaining to the patient that is specified by the user is saved as a Key/Value pair in a database, the Key corresponding to the selection in step (A)(ii) and the Value corresponding to the selection in step (A)(v).

17. The method of claim 11, wherein the selections in step (A)(ii) and (A)(v) are saved as properties of a class object in an object-oriented system.

18. The method of claim 11, wherein the anatomical image comprises an organ or organ system selected from the group of organs and organ systems consisting of the heart, the circulatory system, the respiratory system, the kidneys, the digestive system, the skeletal system and the central nervous system.

19. The method of claim 11, wherein the data is electronically communicated from the computing device, over the Internet, to the server.

20. A method of specifying and saving medical information pertaining to a patient in an electronic medical record in a medical healthcare computer system in which patient medical records are stored and updated, comprising the steps of:
  (a) first,
    (i) presenting on a touch sensitive display of a handheld wireless computing device, for view by a user, a first anatomical image representing at least a portion of a human body;
    (ii) receiving, on the handheld wireless computing device, first user input corresponding to touching by the user on the display of a first area of the first anatomical image representing a selection by the user of a first body part of the first anatomical image presented on the display;
    (iii) determining, based on the received first user input corresponding to selection by the user of a first body part of the first anatomical image, a first set of pictorial images associated with the selected first body part that are each symbolic of a different value associated with the first body part, wherein a combination of
      (A) the first body part of the first anatomical image of the human body selected by the user, and
      (B) one of the pictorial images of the first set of pictorial images symbolic of different values associated with the body part,
    uniquely represents a predefined textual description of medical information;
    (iv) responsive to receiving the first user input, presenting on the display of the handheld wireless computing device, for view by the user,
      (i) a text descriptor corresponding to the first body part, and
      (ii) the determined first set of pictorial images,
    (v) receiving, on the handheld wireless computing device, second user input corresponding to touching by the user on the display of an area representing a selection by the user of one of the presented pictorial images in the first set of pictorial images,
    whereby a first predefined textual description of medical information is specified by the user pertaining to the patient without typing by the user; and
  (b) presenting, on the display of the handheld wireless computing device, for view by the user, the first predefined textual description of medical information;
  (c) thereafter,
    (i) receiving, on the handheld wireless computing device, third user input corresponding to touching by the user on the display of a second area of the first anatomical image representing a selection by the user of a second body part of the first anatomical image presented on the display;
    (ii) determining, based on the received third user input corresponding to selection by the user of a second body part of the first anatomical image, a second set of pictorial images associated with the selected second body part that are each symbolic of a different value associated with the second body part, the second set of pictorial images being different than the first set of pictorial images, wherein a combination of
      (A) the second body part of the first anatomical image of the human body selected by the user, and
      (B) one of the pictorial images of the second set of pictorial images symbolic of different values associated with the body part,
    uniquely represents a predefined textual description of medical information;
    (iii) responsive to receiving the third user input, presenting on the display of the handheld wireless computing device, for view by the user, the determined second set of pictorial images;
    (iv) receiving, on the handheld wireless computing device, user input corresponding to touching by the user on the display of an area representing a selection by the user of one of the presented pictorial images in the second set of pictorial images,
    whereby a second predefined textual description of medical information is specified by the user pertaining to the patient without typing by the user;
  (d) presenting, on the display of the handheld wireless computing device, for view by the user, the second predefined textual description of medical information; and
  (e) electronically communicating, from the handheld wireless computing device, to a server in the medical healthcare computer system in which patient medical records are stored and updated for storing in association with an electronic medical record of the patient,
    (i) data associated with the first and second user input as a first key-value pair corresponding to the first predefined textual description, and
    (ii) data associated with the second and third user input as a second key-value pair corresponding to the second predefined textual description
  (f) wherein the computing device comprises a handheld wireless computing device having a touch sensitive display; and
  (g) wherein the medical information pertaining to the patient is specified by the user by performing said steps without typing by the user.

* * * * *